(12) United States Patent
Blyakhman

(10) Patent No.: US 6,547,775 B1
(45) Date of Patent: Apr. 15, 2003

(54) ATRAUMATIC BLOOD SUCTION SYSTEM

(75) Inventor: Yakov A. Blyakhman, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/425,066

(22) Filed: Oct. 21, 1999

Related U.S. Application Data

(60) Provisional application No. 60/105,252, filed on Oct. 22, 1998.

(51) Int. Cl.[7] ............................................. A61M 31/00
(52) U.S. Cl. ........................................ 604/505; 604/67
(58) Field of Search .............................. 604/6.11, 6.15, 604/6.16, 66, 67, 247, 151–154, 902, 505

(56) References Cited

U.S. PATENT DOCUMENTS

| | | |
|---|---|---|
| 3,834,388 A | 9/1974 | Sauer et al. |
| 4,062,360 A | 12/1977 | Bemtley |
| 4,205,677 A | 6/1980 | Engstrom |
| 4,416,658 A | 11/1983 | Numazawa |
| 4,435,170 A | 3/1984 | Laszcower |
| 4,540,399 A | 9/1985 | Litzie et al. |
| 4,599,093 A | 7/1986 | Steg, Jr. |
| 4,642,097 A | 2/1987 | Siposs |
| 4,706,687 A | 11/1987 | Rogers |
| 4,735,606 A | 4/1988 | Davison |
| 4,828,543 A | 5/1989 | Weiss |
| 4,838,281 A | 6/1989 | Rogers |
| 4,976,682 A | 12/1990 | Lane |
| 5,055,198 A | 10/1991 | Ramakrishna |
| 5,195,995 A | 3/1993 | Walker |
| 5,354,268 A | 10/1994 | Peterson |
| 5,385,540 A | 1/1995 | Abbott ............... 604/6.11 |
| 5,401,255 A | 3/1995 | Sutherland |
| 5,411,472 A * | 5/1995 | Steg, Jr. et al. ............ 604/4.11 |
| 5,423,738 A | 6/1995 | Robinson |
| 5,441,482 A | 8/1995 | Clague |
| 5,520,652 A | 5/1996 | Peterson |
| 5,531,712 A | 7/1996 | Malcom |
| 5,571,081 A | 11/1996 | Adhoute |
| 5,573,502 A | 11/1996 | LeCocq |
| 5,588,816 A | 12/1996 | Abbott |
| 5,645,531 A | 7/1997 | Thompson |
| 5,984,892 A * | 11/1999 | Bedingham .............. 604/67 |

FOREIGN PATENT DOCUMENTS

| | | |
|---|---|---|
| FR | 2 371 202 | 3/1978 |
| WO | WO 86/03832 | 7/1986 |
| WO | WO 97/14451 | 4/1997 |
| WO | WO 98/10810 | 3/1998 |

* cited by examiner

*Primary Examiner*—Anhtuan T. Nguyen
(74) *Attorney, Agent, or Firm*—Thomas G. Berry; Daniel W. Latham

(57) ABSTRACT

An automatic control system and methods of automatic control for reducing the blood/air interface for suction from the left ventricle and/or operating field are provided by the present invention. A system in accord with the present invention will have a pressure sensor or monitor, a pump, and a bubble or air sensor to detect the ratio of air-to-blood in the sucker lines. The system will also have a processing means connected to the pressure sensor, pump, and air sensor for automatically adjusting the pump speed in response to the sensed pressure and/or the sensed air-to-blood ratio, and may have a display and the appropriate manual controls to manually adjust the pump speed also connected to the processing means. A method in accord with the present invention will provide for the sensing of the pressure and the air-to-blood to blood ratio and adjusting the pump speed in accord therewith so as to continuously maintain a suction level that will be adequate to remove the necessary and desired amount of blood without damage to surrounding tissue. In particular, the system will used sensed air-to-blood ratios to adjust the pump speed to desired levels so as to maintain a continuous suction at low pressure levels, varying the pump speed as needed to do so, as opposed to the single speed, high pressure provided by present day blood collection systems.

36 Claims, 1 Drawing Sheet though there may be little blood in the lines or tubes and a great amount of air or gas, the collection device will continue to suck at a high pressure. Suction of blood mixed with air can cause significantly greater hemolysis than suction of blood alone. Thus, increasing the roller pump speed to suck a larger volume of blood more quickly is likely to bring more air into the sucker line to react with the blood in the line, thereby causing more damage to the blood. Using current technology roller pumps for blood removal thus strikes a compromise between a preferred suction level for the rapid removal of blood from the operating field and the possibility of damage to the blood. That is, if the perfusionist reduces the roller pump speed, then the surgeon will have to take longer to remove any large pool of blood in the operating field, thereby lengthening the operation and the increasing the possibility of less desirable outcomes to the surgery. Increasing the speed to reduce the time spent in surgery, however, can result in damage to the blood.

ATRAUMATIC BLOOD SUCTION SYSTEM

This application claims the benefit of provisional patent application No. 60/105,252 filed Oct. 22, 1998.

TECHNICAL FIELD

This invention relates to a generally to systems and methods for suctioning liquids and particularly to a system and a method for suctioning blood that reduces the potential for trauma to blood and to cardiac tissue during surgical procedures.

BACKGROUND OF THE PRESENT INVENTION

Blood collection during surgery is a commonplace and necessary procedure. Blood collection is typically performed to remove blood from the operating or surgical field to provide the surgeon with a clear view of the body and its organs. In addition, during a procedure such as an open heart surgery, blood is also collected to remove blood from the left ventricle. Blood removed from either location is often referred to as "surgical blood".

The standard blood collection device is a roller pump operated at a constant speed or rotation rate to provide suction within various "suction" or "sucker" lines applied to the surgical field to collect the blood. These roller pumps lack the ability to detect either high levels of pressure or high levels of suction. The pumps also have no method of or apparatus for detecting the relative amounts of air and liquid in the lines.

Blood is removed from the operating field by using a roller pump to drive or apply a vacuum to a sucker—line typically plastic tubing—having a sucker tip on its distal end. To increase the volume of blood and the quickness with which the blood can be removed from the operating field, the perfusionist will increase the speed of the roller pump and thus will increase the amount of suction at the sucker tip on the distal end of the sucker line. Conversely, reducing the roller pump speed will reduce the suction and the speed with which a certain volume of blood can be removed from the operating field.

The use of standard roller pumps is known to have several problems associated therewith. First, currently used systems for blood collection typically operate at high negative pressures independently of the presence or absence of gas within the lines. Thus, even Second, current devices can allow the blood to stagnate within the sucker lines, which can lead to hemolysis also. This occurs because the current devices operate continuously at high pressures. Thus, to avoid damage to tissue from the continuous negative pressure in the sucker tip, the suction is either turned off or the sucker tip is removed from the operating field, allowing it to draw air directly into the sucker line. If the suction is turned off, then there is no longer any negative pressure available to move the blood in the line further therethrough, thus allowing the blood to stagnate.

Third, most of the devices, as noted, use roller pumps. These devices compress blood filled tubing to pump the blood, which can destroy or damage the blood cells.

Fourth, as noted, the devices are used at high pressures regardless of the presence of air in the collection tubes. When the sucker tip or cannula contacts tissue or an all blood solution, the negative pressure increases suddenly. The increase in negative pressure creates sheer and traumatizes the blood at the collection site, that is, it increases the risk of hemolysis.

Fifth, removing blood from the left ventricle with too high of a suction level can damage the heart. Currently, cardiac damage is hopefully avoided through the utilization of a three-way valve in the suction line that opens to air at a predetermined trigger level, such as when the suction level reaches about 180 mm Hg. When the trigger pressure level is reached, the valve opens to allow air into the line and to prevent the suction level from generally exceeding the trigger level. The three-way valve just described is not a complete remedy to the problem of too much suction, however, since the air introduction, while reducing the potential for damage to the heart, creates a direct air-blood interface that can potentially damage the blood.

Systems that employ suction to remove surgical blood from a surgical field include those disclosed in the following US Patents, all of which are incorporated into this application by reference in their entireties: U.S. Pat. No. 3,834,388 (Sauer); U.S. Pat. No. 4,062,360 (Bentley); U.S. Pat. No. 4,205,677 (Engstrom); U.S. Pat. No. 4,416,658 (Numazawa et al.); U.S. Pat. No. 4,435,170 (Laszczower); U.S. Pat. No. 4,540,399 (Litzie et al.); U.S. Pat. No. 4,599,093 (Steg, Jr); U.S. Pat. No. 4,692,097 (Siposs); U.S. Pat. No. 4,706,687 (Rogers et al.); U.S. Pat. No. 4,735,606 (Davison); U.S. Pat. No. 4,828,543 (Weiss et al.); U.S. Pat. No. 4,838,281 (Rogers et al.); U.S. Pat. No. 4,976,682 (Lane et al.); U.S. Pat. No. 5,055,198 (Shettigar); U.S. Pat. No. 5,195,995 (Walker); U.S. Pat. No. 5,354,268 (Peterson et al.); U.S. Pat. No. 5,385,540 (Abbott et al.); U.S. Pat. No. 5,401,255 (Sutherland et al.); U.S. Pat. No. 5,411,472 (Steg, Jr. et al.); U.S. Pat. No. 5,423,738 (Robinson et al.); U.S. Pat. No. 5,441,482 (Clague et al.); U.S. Pat. No. 5,520,652 (Peterson); U.S. Pat. No. 5,531,712 (Malcolm et al.); U.S. Pat. No. 5,645,531 (Thompson et al.); U.S. Pat. No. 5,573,502 (LeCocq et al.); U.S. Pat. No. 5,571,081 (Adhoute); and U.S. Pat. No. 5,588,816 (Abbott et al.).

It would be desirable to have a system and method for removal of surgical blood that would reduce the potential for damage to the heart and blood during its use. In particular, it would be desirable to have a system and method for removal of surgical blood that would allow the perfusionist or other user to employ continuous suction at a low negative pressure while still satisfying the need for removal of blood in a timely and complete manner.

SUMMARY OF THE PRESENT INVENTION

It is an object of the present invention to provide new and useful systems and methods that are not subject to the foregoing deficiencies.

It is another object of the present invention to provide a system for suctioning blood that is less likely to create damage to either the heart or the blood during use.

It is still another object of the present invention to a new and useful method of suctioning surgical blood that is less likely to create damage to either the heart or the blood during its use.

An automatic control system and methods of automatic control for reducing the blood/air interface for suction from the left ventricle and/or operating field enable the achievement of the foregoing objects of the present invention. A system in accord with the present invention provides continuous suction at a low negative pressure and enables the operator to maintain a constant, predetermined pressure by adjusting the roller pump speed in response to sensed pressures in the sucker line. A system in accord with the present invention will have a pressure sensor or monitor, a pump, and a bubble or air sensor to detect the ratio of air-to-blood in the sucker lines. The system will also have a processing means connected to the pressure sensor, pump, and air sensor for automatically adjusting the pump speed in response to the sensed pressure and/or the sensed air-to-blood ratio, and may have a display and the appropriate manual controls to manually adjust the pump speed also connected to the processing means.

A method in accord with the present invention will provide for the sensing of the pressure and the air-to-blood to blood ratio and adjusting the pump speed in accord therewith so as to continuously maintain a suction level that will be adequate to remove the necessary and desired amount of blood without damage to surrounding tissue. In particular, the system will used sensed air-to-blood ratios to adjust the pump speed to desired levels so as to maintain a continuous suction at low pressure levels, varying the pump speed as needed to do so, as opposed to the single speed, high pressure provided by present day blood collection systems.

The system in accord with the present invention will be operable in one or more modes, such as a manual, automatic, constant vacuum, "blood coming" detection, blood/air percentage detection; variations to automatic mode, and may include filtering features.

DISCLOSURE OF THE INVENTION

Figure 1:
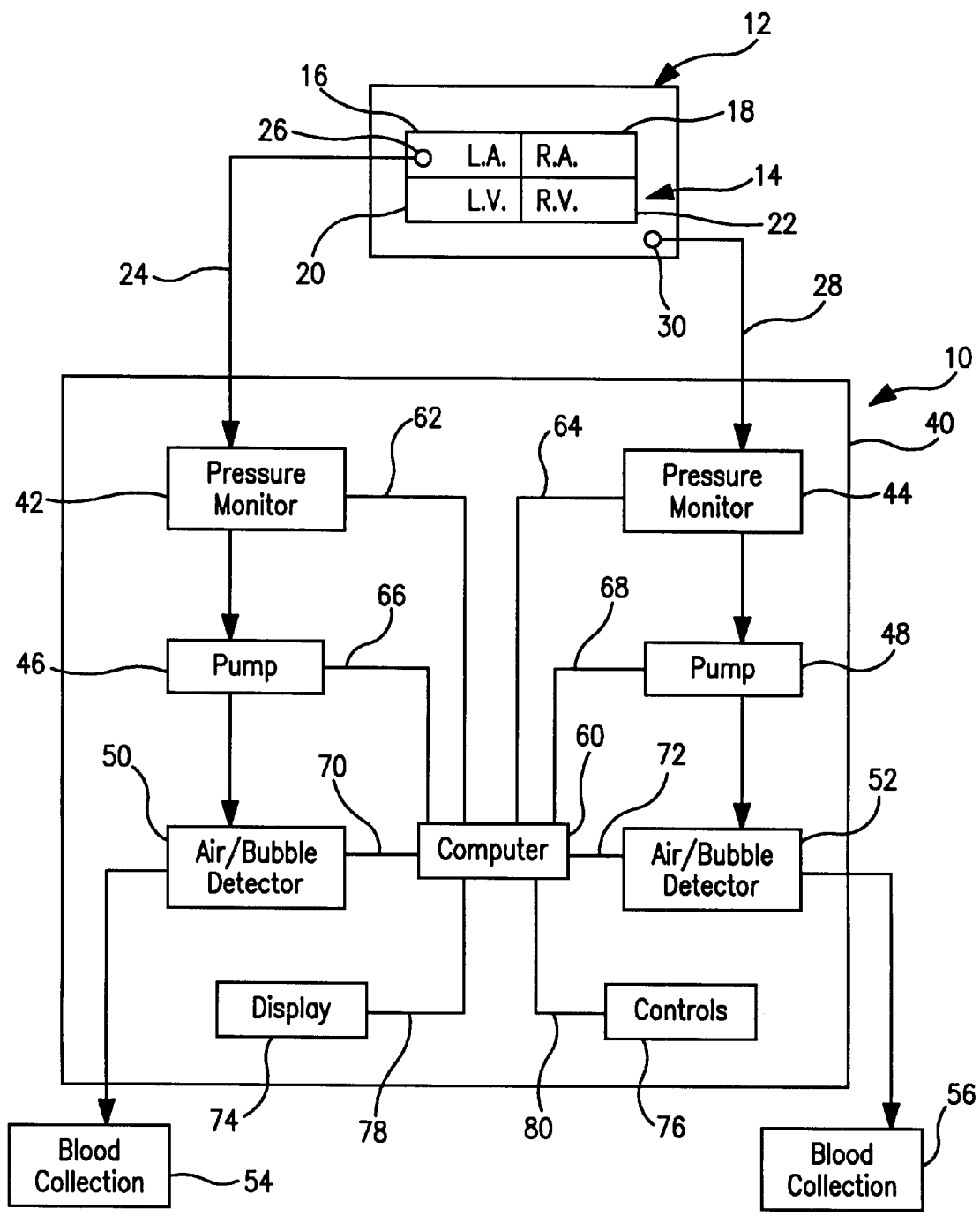
FIG. 1 is a schematic view of a blood collection system in accord with the present invention.

FIG. 1 shows in a schematic view a blood collection system 10 in accord with the present invention and particularly how such a device is used during open heart surgery. The chest cavity 12 of a patient is shown along with the patient's heart 14, including the left and right atria 16, 18, respectively, and the left and right ventricles, 20, 22 respectively. A sucker line 24 having a sucker tip 26 at its distal extends from the left atrium 16 of the heart 14 to the system 10 for the removal of blood entering that heart chamber. Similarly, a second sucker line 28 having a sucker tip 30 at its distal end extends from the chest cavity 12 to the system 10 for removal of blood pooling within the chest cavity 12 or elsewhere in the operating field. The proximal ends of the lines 24, 28 are attached to the system 10. While the present invention can be applied to any blood collection system, reference is made to the Medtronic CSS 990 Cardioplegia Safety System is described in the "CSS 990 Operator and Reference Manual" Rev. A00, previously incorporated by reference into provisional patent application No. 60/076,765 of Michael P. Petersen filed Mar. 4, 1998 for specific and extensive details of the operation of such system as well as its detailed construction.

The system 10 will generally include a housing 40. Each sucker line 24, 28 will feed into a pressure monitor 42, 44, respectively, a pump 46, 48, which may be a roller or pertistaltic pump, respectively, and a bubble or air detector 50, 52, respectively. After passing through the bubble detectors 50, 52, the blood will be delivered to respective collectors 54, 56.

The pressure monitors 42, 44, pumps 46, 48, and bubble detectors 50, 52 will each be electronically connected to a computer, microprocessor, or other processor 60 via lines 60, 62, 64, 66, 68, 70, and 72. The computer 60 may also be connected to a display 74, which may be a computer monitor or any other known display device, and appropriate manual pump speed controls, such as rotary control knobs, 76 via lines 78 and 80, respectively, enabling individual manual control of the pumps 46 and 48 as desired. That is, the display 74 can be configured to display operating parameters relative to one or both of the suction lines 24, 28 and the respective monitors, pumps, and sensors associated with each line. Similarly, controls 76 may include separate controls for each of the lines, allowing each of them to be individually controlled. The display can, as is well known in the art, be configured to provide both numeric and/or graphical data simultaneously and in the desired units of measurement. In this manner, then, the operating performance of the system 10 can be visually and aurally displayed as desired, including such parameters as pump speed, line pressure, blood volume collected, or any other desired parameter related to the operation of the system 10 and the patient. An aural display may be provided to provide aural indications of certain predetermined warning conditions, for example.

System 10 will operate to sense the line pressure with the monitors 42, 44 and the presence of air in the lines 24, 28. This information will be provided to the computer 60 and, together with the current pump speed, a revised pump speed will be calculated and provided to the pumps 46, 48.

The system 10 will enable a user to employ continuous suction at a low negative pressure. Sensors 50, 52 will detect the presence or absence of air in the lines 24, 28. The system air sensors detect air or liquid in the line continuously. The air/blood ratio is determined by an appropriate algorithm that integrates sensor output on over time. Instead of using exact time as an integrating parameter, time as a function of pump speed can be used instead. When the air-to-blood ratio is high, the negative pressure remains low. When the ratio of air-to-blood decreases, the negative pressure will be automatically increased by the provision of the appropriate signal from the computer 60 to the pumps 46, 48 as needed. The negative pressure may be increased until a predetermination of air-to-blood is reached, that is, the air-to-blood ratio levels off or begins to increase again or until the negative pressure, i.e, suction level, reaches some predetermined or user set negative pressure limit.

Therefore, when there is a high volume of air and a low volume of blood, pressure is low. When there is a high volume of blood and a low volume of air, pressure is higher. The automatic response of the system 10 to measured air-to-blood ratios will aid in minimizing hemolysis during suction. Because the system 10 can safely maintain a steady low level of negative pressure with air in the sucker lines 24, 28, the system 10 can be always be left running as opposed to present day systems which are either on at high pressures or off. With the system 10, blood continues to move through the tubing at all times, thus helping to prevent stagnation. To accomplish this, the system 10 can be operated manually, with the operator adjusting the flow rate manually using the controls 76. Additionally, the system 10 can be set to operate automatically such that the pressure is maintained at a constant by adjusting either the pump speed or the flow rate as needed to maintain the predetermined constant pressure.

Where the sucker tip 26, 30 directly engages tissue, there can be a sudden increase in negative pressure that is potentially damaging to the tissue. This form of damage can be avoided again by the present invention. First, when the air sensors 50 or 52 detect a decrease in the air-to-blood ratio, and therefore an increase in the blood, the pump speed will increase gradually. The gradual increase in the pump speed results in a gradual increase in suction, thus mitigating blood shear and potential damage. This can be accomplished in an automatic manual mode using the present invention. First, the operator of the system 10 can set the desired flow rate within a range of say 0 to 400 milliliters per minute. Typically, the user will operate controls 76 to adjust the flow rate to a desired level to create an initial low suction rate, which may be about 50 milliliters per minute. Operation of the pump for the appropriate suction line will continue at this rate until a decrease in the air volume passing through the sucker lines is detected. When a predetermined reduction in air flow over a predetermined time period is detected, say a ten percent reduction for at least one second, then there has been a concomitant ten percent increase in blood flow. The pump 46 or 48 will be commanded by the computer 60 to increase its speed to increase the flow rate and blood removal rate, say to 175 milliliters per minute. This flow rate will then be maintained until the percentage of air detected by the sensors 50, 52 decrease by a predetermined amount, say 50%. At this point in time, the flow rate will automatically be decreased by an appropriate signal from the computer 60 to the appropriate pump 46, 48.

Alternatively to the mode described above, the present invention contemplates that the operator may automatically set a maximum negative pressure or suction level. The computer 60 can be programmed to enable the operator to set both pressure alert and pressure alarm levels. When the pressure in a sucker line reaches the pressure alert level, the system 10 may provide either an audible alert tone or a flashing alert light or both. Similarly, when the alarm level is reached, the pump will be automatically shut off by an appropriate command from the computer 60, which has been receiving the pressure signals from the appropriate pressure monitor. In addition, an alarm tone can be generated and/or an alarm light can be flashed. In both instances, the signals will provide the operator with notice that an unusual pressure condition has been reached, for example, a condition caused by the sucker lines becoming twisted or plugged.

To further avoid damage to blood and tissue, the present invention includes sucker tips or cannulae 26 and or 30 being formed from a soft, tip to aid in the prevention both tissue damage and sudden pressure build-ups, unlike the present tips which are usually formed of a hard plastic material.

More generally, the present invention can be operated in a number of operating modes, including a manual mode, a constant vacuum or pressure mode, or an automatic mode. In the manual mode of operation, the suction level is controlled by the user through the manual adjustment of the pump speed by turning a control knob. The inventive system monitors pressure (suction) in the line, enabling the operator the option of setting a high vacuum level alert (e.g., audible alarm but pumping continues) and/or alarm (audible alarm and motor stops). Should the negative pressure exceed the vacuum alert or alarm levels then a vacuum alert or alarm would occur.

The constant vacuum mode allows the operator to control directly the suction level applied to the surgical field. The is accomplished by setting the desired pressure level using the appropriate controls, which as is well know in the art can take many forms of equal facility, such as a rotor knob on the controls 76. System 10 will then monitor the pressure in the lines using the pressure sensors and adjust the pump speed for that line as is needed to maintain the desired pressure, that is, pressure is adjusted by adjusting the flow rate in the lines. In contrast, in the manual mode the user sets the desired flow rate by setting the pump speed, In the constant vacuum mode, the pressure level is set and the flow rate and thus the pump speed are varied to obtain the predetermined suction level. Certain clinical situations, such as the removal of blood from small spaces in the heart or brain, exist where controlling by pressure is desirable.

In the automatic mode, the operator will set some small initial, predetermined value of a low pump speed as noted previously, thereby keeping the vacuum pressure at a very low level. Regardless of the placement of the sucker tip, then, there would be very little hemolysis and there also would be prevention of tissue trauma due to the low level of suction. When an increase in blood flow is detected by the decrease in the amount of air detected by the air sensors, the computer will, through the appropriate algorithm—a "blood coming" algorithm—detect it and begin to increase the pumping rate. The "blood coming detection" method detects blood by monitoring line pressure in a suction line. As the level of blood increases in the suction line, the monitor will detect an increase in pressure level. The system thus helps prevent hemolysis since it sucks at a low rate when air is present while increasing the suction rate when more blood is present.

More specifically, if the air detector will not detect at least a predetermined blood level, say 50%, after a predetermined period of time, the system will return to a slow speed and low suction level. If the air detector does detect blood at or greater than the predetermined level, the system will maintain the high pumping speed, and thus the high flow rate, until it pumps all blood out and the air detector shows a predetermined level of air, such as at least 98%, in the suction stream. After this the pump will be commanded to reduce its pumping flow rate to a low level, that is, where a roller pump is used it will slow down to a small speed. High vacuum level alerts and/or alarms could be also used in this mode. In this automatic mode, hemolysis is lowered and tissue is protected in an automatic way, freeing the perfusionist to concentrate on delivery of cardioplegia solution, which is the most crucial task, and not removal of blood.

Variations to the automatic mode also exist. For example, the computer can be programmed to provide that the suction line is operated at two different speeds: a low speed (or no speed) when not sucking, and at a high speed for quick suction. The change in speed is controlled at the correct time for the correct duration. Possible variations on the above method of operation include enabling the operator to select the low speed or pumping flow rate point when the automatic mode is initiated This point could be preset. The preset value could either be set by software or user settable. In addition, a manually operated switch could be placed on the sucker tip to momentarily block the flow, which in turn would be detected by the pressure sensor as an increase in suction. The computer 60 would then direct the pump to turn up the flow rate. This would allow the surgeon to increase the speed of the sucker directly.

Furthermore, the high pumping speed could either be preset as a flow value or preset as a suction level or a combination of both (i.e., do not exceed 1 liter per minute or 100 mm Hg suction). The preset values could either be set by software or user settable.

The above method relies on both suction levels and percent air before the pumping speed is decreased. The method could either be a simple step, such as running at a high speed for 10 seconds or it could be controlled by controlling the suction, such as running at high speed until the suction drops indicating a clear line. Additionally, the controlling parameter could be the amount of air or fluid detected in the line, such as run the pump at high speed until the line is 98% air. Finally, a combination of some or all of the above could be used to control the pressure and flow rates.

Lastly, as a final variation, the transition from low to high pump speeds or high to low pump speeds could be manually initiated by the perfusionist or surgeon by operation of a switch (probably push button) either on the equipment or remotely (such as a button on the cannula).

To set the various modes, a single switch could be provided that would allow the user to toggle between the various modes allowing a single control know to be used to control the desired parameter. For example, a single switch could be used to toggle between the manual, constant pressure, and automatic modes. Or separate buttons could be provided on the controls 76 to allow the user to select the desired operating mode.

It will be understood that various filtering techniques will be used to eliminate system noise. System noise can come from a variety of sources, but the most significant source of noise comes from the interaction between the rollers and the fluid in the tube. Low pass filters can be used for to reduce the noise, though a comb filter is preferred.

The present invention having thus been described, other modifications, alterations, or substitutions may now suggest themselves to those skilled in the art, all of which are within the spirit and scope of the present invention. It will be understood that a system in accord with the present invention need not be a dual suction system as shown herein and that a system having one or more than one suction lines would fall within the scope of the attached claims. Furthermore, it will be understood that while the present invention has been described with reference to open heart surgery that it may be useful in other clinical applications. Additionally, it will be understood that the predetermined response levels as well as predetermined flow rates and pressure levels will vary based upon various patient factors such as the age of the patient and the tissue in the surgical field. It is therefore intended that the present invention be limited only by the scope of the attached claims below.

I claim:

1. A method of transporting surgical blood under vacuum, comprising:

providing an suction line having a suction tip for engaging the surgical blood;

providing a pump for supplying a negative pressure to said suction line;

providing a negative pressure on the suction line to suction blood by operating the pump at a first pump speed;

sensing the air-to-blood ratio in the suction line;

sensing a negative pressure level in the suction line; and operating the pump at a second, different pump speed in response to the sensed air-to-blood ratio and the sensed negative pressure level.

2. The method of claim 1 wherein said second pump speed is provided in response to a predetermined change in the sensed air-to-blood ratio of about ten percent.

3. The method of claim 1 further including continuously monitoring the air-to-blood ratio when the sensed air-to-blood ratio reaches a predetermined maximum air-to-blood ratio.

4. The method of claim 3 wherein said predetermined maximum air-to-blood level is about 98%.

5. The method of claim 1 wherein said pump is operated to provide a second pump speed to provide a predetermined minimum sensed negative pressure level when said predetermined maximum sensed air-to-blood ratio is reached.

6. The method of claim 5 wherein said predetermined minimum sensed negative pressure level is at a flow rate of about 50 milliliters per minute.

7. The method of claim 1 wherein said second pump speed is less than said first pump speed in response to an increase in the sensed air-to-blood ratio.

8. The method of claim 7 wherein said second pump speed is also determined in response to a predetermined minimum sensed negative pressure level.

9. The method of claim 8 wherein said predetermined minimum sensed pressure level is at a flow rate of about 50 milliliters per minute.

10. A method for removing blood during surgery from the surgical field, said method including:

providing a suction line and a pump for supplying a negative pressure to said suction line;

establishing a predetermined desired minimum negative pressure level for the suction line;

providing suction in the surgical field with a suction line;

monitoring the negative pressure in the suction line;

establishing a predetermined desired maximum air-to-blood ratio in the suction line;

monitoring the air-to-blood ratio in the suction line; and adjusting the speed of the pump in response to the monitored negative pressure and the monitored air-to-blood ratio.

11. The method of claim 10 wherein said negative pressure is provided by a roller pump attached to the surgical line.

12. The method of claim 11 wherein said adjustment is provided by changing the speed of the roller pump.

13. The method of claim 10 wherein the operation of the pump is adjusted by increasing pump speed in response to a decrease in the monitored negative pressure level.

14. The method of claim 10 wherein the operation of the pump is adjusted by decreasing pump speed in response to an increase in the monitored negative pressure level.

15. A method for reducing hemolysis and tissue damage during surgery, said method comprising:

collecting blood with a suction line;

providing a pump for supplying a negative pressure to said suction line;

monitoring the air-to-blood ratio in the suction line;

monitoring the negative pressure in the suction line; and adjusting the speed of the pump in response to monitored changes in negative pressure and in response to monitored changes in the air-to-blood ratio.

16. The method of claim 15 wherein the operation of the pump is adjusted by decreasing pump speed in response to a monitored increase in the air-to-blood ratio.

17. The method of claim 15 wherein the operation of the pump is adjusted by increasing pump speed in response to a monitored decrease in the air-to-blood ratio.

18. A method of transporting surgical blood under vacuum, comprising:
providing an suction line having a suction tip for engaging the surgical blood;
providing a pump for supplying a negative pressure to said suction line;
providing a negative pressure on the suction line to suction blood by operating the pump at a first, low pump speed;
sensing the air-to-blood ratio in the suction line;
sensing a negative pressure level in the suction line; and
operating the pump at a second, higher pump speed in response to a decrease in sensed air-to-blood ratio and an increase in sensed negative pressure level.

19. The method of claim 18 wherein said second, higher pump speed is provided in response to a predetermined decrease in the sensed air-to-blood ratio of about ten percent.

20. The method of claim 18 further including continuously monitoring the air-to-blood ratio when the sensed air-to-blood ratio reaches a predetermined maximum air-to-blood ratio.

21. The method of claim 20 wherein said predetermined maximum air-to-blood level is about 98%.

22. The method of claim 20 wherein said pump is operated to provide a pump speed to provide a predetermined minimum sensed negative pressure level when said predetermined maximum sensed air-to-blood ratio is reached.

23. The method of claim 22 wherein said predetermined minimum sensed negative pressure level is at a flow rate of about 50 milliliters per minute.

24. The method of claim 18 wherein said pump is operated to provide a third, lower pump speed than said second pump speed after a predetermined period of time.

25. The method of claim 18 wherein an alarm is provided in response to the detection of a predetermined maximum sensed negative pressure level.

26. The method of claim 18 wherein said pump is stopped in response to the detection of a predetermined maximum sensed negative pressure level.

27. A method for removing blood during surgery from the surgical field, said method including:
providing a suction line and a pump for supplying a negative pressure to said suction line;
establishing a predetermined desired minimum negative pressure level for the suction line;
providing suction in the surgical field with a suction line;
monitoring the negative pressure in the suction line;
establishing a predetermined desired maximum air-to-blood ratio in the suction line;
monitoring the air-to-blood ratio in the suction line; and
increasing the speed of the pump in response to an increase in the monitored negative pressure and a decrease in the monitored air-to-blood ratio.

28. The method of claim 27 wherein said negative pressure is provided by a roller pump attached to the surgical line.

29. The method of claim 27 wherein the operation of the pump is adjusted by decreasing pump speed in response to sensing a monitored negative pressure at the level of a predetermined maximum pressure level.

30. The method of claim 27 wherein said predetermined desired minimum negative pressure level is at a flow rate of about 50 milliliters per minute.

31. The method of claim 27 wherein said pump speed is decreased after a predetermined period of time.

32. The method of claim 27 wherein an alarm is provided in response to the detection of a predetermined maximum sensed negative pressure level.

33. The method of claim 27 wherein said pump is stopped in response to the detection of a predetermined maximum sensed negative pressure level.

34. A method for reducing hemolysis and tissue damage during surgery, said method comprising:
collecting blood with a suction line;
providing a pump for supplying a negative pressure to said suction line;
establishing a predetermined desired maximum negative pressure level for the suction line;
monitoring the air-to-blood ratio in the suction line;
monitoring the negative pressure in the suction line; and
adjusting the speed of the pump in response to monitored changes in negative pressure and in response to monitored changes in the air-to-blood ratio such that the negative pressure in the suction line is maintained at a level below the perdetermined desired maximum negative pressure level.

35. The method of claim 34 wherein the operation of the pump is adjusted by decreasing pump speed in response to a monitored increase in the air-to-blood ratio.

36. The method of claim 34 wherein the operation of the pump is adjusted by increasing pump speed in response to a monitored decrease in the air-to-blood ratio.

* * * * *